United States Patent [19]

Wu et al.

[11] Patent Number: 4,661,913
[45] Date of Patent: Apr. 28, 1987

[54] APPARATUS AND METHOD FOR THE DETECTION AND CLASSIFICATION OF ARTICLES USING FLOW CYTOMETRY TECHNIQUES

[75] Inventors: Hai-Ping Wu, Chapel Hill; Burton H. Sage, Jr., Raleigh; Robert F. Adrion, Cary, all of N.C.

[73] Assignee: Becton, Dickinson and Company, Franklin Lakes, N.J.

[21] Appl. No.: 649,449

[22] Filed: Sep. 11, 1984

[51] Int. Cl.$^4$ .................. G06F 15/46; G01N 15/00
[52] U.S. Cl. ................................ 364/500; 356/442; 364/550; 364/554; 364/555; 382/6; 422/68; 436/63
[58] Field of Search .................. 364/497–500, 364/550, 554, 555; 356/39, 433, 436, 441, 442; 382/6, 36; 436/63; 422/68; 250/461.2

[56] References Cited

U.S. PATENT DOCUMENTS

| | | | |
|---|---|---|---|
| 4,225,229 | 9/1980 | Gohde | 356/39 |
| 4,243,318 | 1/1981 | Stöhr | 356/39 |
| 4,284,355 | 8/1981 | Hansen et al. | 356/39 |
| 4,295,199 | 10/1981 | Curry et al. | 364/555 |
| 4,338,024 | 7/1982 | Bolz et al. | 356/39 |
| 4,338,811 | 7/1982 | Miyagi et al. | 364/498 |
| 4,352,558 | 10/1982 | Eisert | 356/39 |
| 4,468,742 | 8/1984 | Jenden et al. | 364/497 |
| 4,514,816 | 4/1985 | Ollus et al. | 364/555 |
| 4,538,733 | 9/1985 | Hoffman | 356/39 |
| 4,541,719 | 9/1985 | Wyatt | 364/555 |
| 4,581,334 | 4/1986 | Kirchanski et al. | 356/39 |

OTHER PUBLICATIONS

*Scientific American* 234(3):108, 1976, "Fluorescence-Activated Cell Sorting", Herzenberg et al, pp. 108–117.

*Adv. Computers* 12:285–414, 1972, "Parametric & Non-parametric Recognition by Computer...", Prewitt, pp. 285–414.

*Anal. Quant. Cytol.* (1979, 1980, 1981), "Numerical Evaluation of Cytologic Data", parts I–VIII, Bartels.

*Flow Cytometry & Sorting*, "Cytometric Data Processing", Sharpless, Pub John Wiley & Sons, 1979, pp. 359–379.

*J. Histochem. Cytochem.*; 27:560, 1978; "Visualization of Multi-Dimensional Spectra in Flow Cytometry", Stohr et al.

*Primary Examiner*—Errol A. Krass
*Assistant Examiner*—Kevin J. Teska
*Attorney, Agent, or Firm*—Richard J. Rodrick

[57] ABSTRACT

This invention concerns a flow apparatus and method for the detection of particles in a sample. Particles are moved, substantially one at a time, in a fluid flow stream. An incident beam of illumination is provided so as to be directed at the particles in the flow stream. Data associated with each moving particle as it passes through the beam of illumination is detected. A class of particles is established, these particles having common characteristics based on the data detected from such class of particles. The data is then stored. Such stored data is compared to data detected from sample particles of an unknown class. A determination is then made that particles from the unknown class belong to the established class as a result of matching respective data.

69 Claims, 12 Drawing Figures

APPARATUS AND METHOD FOR THE DETECTION AND CLASSIFICATION OF ARTICLES USING FLOW CYTOMETRY TECHNIQUES

BACKGROUND OF THE INVENTION

1. Field of the Invention

The present invention relates to an apparatus and method for the detection of particles in a sample, and more particularly, concerns a flow cytometry apparatus and method for the detection and classification of biological particles of interest from a heterogeneous population of biological particles.

2. Description of the Prior Art

Flow cytometry apparatuses rely upon flow of cells or other particles in a liquid flow stream in order to determine one or more characteristics of the cells under investigation. Further, the flow cytometry apparatus is useful for identifying the presence of certain cells or particles of interest, enumerating those cells or particles and, in some instances, providing a sorting capability so as to be able to collect those cells or particles of interest. In a typical flow cytometry apparatus, a fluid sample containing cells is directed through the flow cytometry apparatus in a rapidly moving liquid stream so that each cell passes serially, and substantially one at a time, through a sensing region. Cell volume may be determined by changes in electrical impedance as each cell passes through the sensing region. Similarly, if an incident beam of light is directed at the sensing region, the passing cells scatter such light as they pass therethrough. This scattered light serves as a function of cell shape and size, index of refraction, opacity, roughness and the like. Further, fluorescence emitted by labeled cells, or autofluorescent cels, which have been excited as a result of passing through the excitation energy of the incident light beam is detectable for indentification of cells having fluorescent properties. After cell analysis is performed by the flow cytometry apparatus, those cells that have been identified as having the desired properties may be sorted if the apparatus has been designed with such capability.

Representative flow cytometry apparatuses are described in U.S. Pat. Nos. 3,826,364 and 4,284,412, and in the publication by Herzenberg et al., "Fluoroescence-activated Cell Sorting," *Sci. Am.* 234 (3): 108, 1976.

Rapid quantitative analysis of biological cells is proving very useful in biomedical research and clinical medicine. New flow cytometry apparatuses permit quantitative multiparameter analysis of cellular properties at rates of several thousand cells per second. These instrumentts provide the ability to differentiate among cell types by measuring difference between them. Differentiation is based upon the characteristics of fluoroescence, which may be used to detect functional differences of the cells, and light scattering, a function of cell morphology.

Even though advances in flow cytometry techniques have improved cellular analysis, there are still some deficiences in the presently available equipment. For example, flow cytometry techniques may be used to detect the presence of bacteria in human blood, a condition known as bacteremia. Currently accepted diagnostic methods available for detecting bacteremia are based on visual detection of the growth of bacteria in liquid media inoculated with blood samples. Detection of bacteremia by the growth methods is slow, usually requiring two to fourteen days. Flow cytometry techniques using specific labeling of the bacteria with fluorescent dyes and procedures of sample preparation, which allow discrimination of residual blood cells, have been studied. At present, once a positive blood culture has been identified, clinical laboratories utilize additional materials, labor, and time in order to obtain bacterial classification/antibiotic senstivity information. These procedures, although effective, are costly and are virtually all dependent upon bacterial growth. Results are not available until hours later, and in most cases overnight or multiday incubation is required. Accordingly, there is a cleary perceived need to increase the speed of this follow-up testing. Such increase in speed could be achieved by the application of flow cytometry techniques to the non-growth classification of bacteria.

Progress in the application of flow cytometry techniques has also been limited by the lack of sophisticated methods of analysis for handling multi-feature data to provide reliable results. Data obtained by flow cytometry apparatuses are almost always displayed in the form of one-dimensional (histogram) and two-dimensional (contour plot, scatter plot) frequency distributions of measured variables. The partitioning of multiparameter data files involves consecutive use of the interactive one- or two-dimensional graphics programs. This procedure is not only cumbersome, but also loses the advantages of processing data in multi-dimensional space, and may obscure a significant subpopulation of cells.

For example, presently available flow cytometry apparatuses have the capability of measuring four features for each of thousands of cells per second. Data processing for cell classification must transform such large sets of multiparameters input data into meaningful experimental measures, and is an extremely complex task. By far the most popular method of data processing has involved the successive use of rectangular windows in two-dimensions to achieve multi-dimensional analysis.

Quantitative analysis of multiparameter flow cytometric data for rapid cell detection consists of two stages: cell class characterization and sample processing. In general, the process of cell class characterization partitions the cell feature space into disjoint regions of cells of interest and cells not to interest. Then in sample processing, each cell is classified in one of the two categories according to the region into which it falls. Careful analysis of the class of cells under study is very important, because good detection performance may be expected only if an appropriate region for the representation of the cells of interest is obtained. Thus, selecting a specific region for a population of cells is the fundamental operation of cellular detection data analysis. But for multiparameter data, the problem of isolating the region of interest in four-dimensional space by visul inspection is an impractical task. A possible solution for this approach is selecting two two-dimensional windows at a time.

Whether four or five parameter rectangular window gating is utilized, most cell clusters exhibit elliptic or ovoid shape in the coordinates space represented by two color fluorescence detection. The major axes of these clusters are often not parallel to the coordinate axes. The ideal boundary for defining such a region is therefore an ellipsoidal or ovoid figure in multidimension space. The rectangular windows for isolating such clusters usually enclose a great deal of open space thereby assigning unwanted background particles as cells of interest, and consequenty introducing classification error.

There appears to be a need for more sophisticated algorithms to improve the analytical capabilities of the flow cytometry apparatuses. There is no known work which attempts to classify "events" measured by flow cytometry equipment using the techniques of pattern recognition.

Pattern recognition is a field concerned with machine recognition of meaningful regularities in noisy or complex environments. It includes the detection and recognition of invariant properties among sets of measurements describing objects or events. In general, the purpose of pattern recognition is to categorize a sample of observed data as a member of a class. A set of characteristics measurements and relations need to be extracted first for the representation of the class, then classification of the data on the basis of the representation may be performed. This approach has been applied to problems from many diverse fields, including some studies in the field of cytology.

One investigator applied pattern recognition methods to leukocyte images obtained by microscopic examination of specially stained blood smears (Prewitt, J. M. S., "Parametric and Nonparametric Recognition by Computer: An Application to Leukocyte Image Processing," *Adv. Computers* 12:25–414, 1972). In the Prewitt publication, five tapes of white cells found in normal human peripheral blood were distinguished on the basis of computer processing of digitized microimages. A similar body by Bartels described attempts to statistically characterize cycltologic "profiles" for normal and abnormal cell populations. Several multivariate analysis methods were used to determine the statistically significant differences among the profiles. Cells could then be classified into these two categories with a high degree or accuracy. (Bartels, T. H., "Numerical Evaluation of Cytologic Data, I–VIII, *Anal. Quant. Cytol.* 1,2,3, (1979, 1980, 1981).

For flow cytometry data processing, little work has been done in applying pattern recognition. In an attempt to match window shapes to cluster outlines in two-dimensional space, one investigator tried to use a quadratic or piecewise-quadratic equation to form a elliptic window (Sharpless, T., "Cytometric Data Processing," in: *Flow Cytometry and Sorting*, Melamed M. R., Mullaney, P. F., Mendelsohn, M. L. (Eds.) John Wiley and Sons, New York, 1979, pages 359–379). The window may be adjusted to fit the cell cluster. Since the power of discrimination is increased when data are anayzed in high dimensional space, other investigators have described hardware and software for three-dimensional graphical analysis, in which ellipsoidal clusters are separated by planes (Stohr, M., and Futterman, G., "Visualization of Multidimensional Spectra in Flow Cytometry," *J. Histochem. Cytochem.* 27-560, 1978). However, it is much more difficult to visualize an anaysis space of more than three dimensions, while flow cytometry data typically contains four parameters for each cell.

In the analysis of biological particles, detection of the particles alone is usually not enough. To be clinically useful, some indication of what particles such as bacteria, are present must also be provided so that the clinician may make decisions regarding probable site of infection and suitable antimicrobial therapy. Presently in clinical laboratories, bacterial classification is usually performed by observing or measuring the results of biochemical reactions between specific reagents and bacteria and/or their metabolic products. This process requires a pure bacterial isolate, may take four to six or more hours, and requires inocula of greater than $10^7$ colony forming units per milliliter (cfu/ml). As it stands now, the classification information cannot be provided until organisms grow to sufficient numbers to provide inocula for the usual procedure. Therefore, decisions based on organisms actually recovered from the patient are only possible in a two or fourteen day timeframe. Waiting for these results may create a high risk of patient morbidity or mortality. In recent practice, early decisions are usually empirical, based upon patient symptoms. So the need for earlier informed decisions regarding antimicrobial therapy remains. To permit earlier informed decisions, methods are needed which allow classificsation at lower concentrations of biological particles and which may, therefore, be accomplished more quickly.

Thus, the present invention is directed to pattern recognition techniques to improve the performance of particle detection and classification using multiparmeter flow cytometric data.

SUMMARY OF THE INVENTION

The apparatus of the present invention for the detection of particles in a sample comprises means for moving particles, substantially one at a time, in a fluid flow stream. An incident beam of illumination is preferably directed at the particles in the flow stream. Light detection means is included for detecting light-related data associated with each moving particle as it passes through the beam of illumination. Means is included for establishing a class of particles having common characteristics in accordance with a pattern of light-related data detected from such class of particles. Means is further included for determining that sample particles from an unknown class belong to the established class responsive to the recognition of the pattern by light-related data detected from the sample particles. Data gathered by electrical or accoustical sensing may also be employed for the pattern recognition techniques described herein.

In another embodiment of this aspect of the invention, a flow cytometry apparatus detects and classifies biological particles of interest from a heterogeneous population of biological particles. In addition to the elements of the apparatus described above, this embodiment includes means for separating the established class into a plurality of subclasses with each subclass having its light-related data stored separately. The comparing means compares such stored data to light data detected from sample particles of an unknown class. Means then determines that particles from the unknown class belong to the established class as a result of matching respective light-related data and identifies the subclasses to which the unknown particles belong.

In another aspect of the present invention, a method detects particles in a sample. The method includes establishing a class of particles having known, common characteristics in accordance with a pattern of data detected from such class of known particles. Data related to the particles may be detected by various techniques, including electrical or accoustical sensing, as well as light characteristics of the particles. Then, the method determines that sample particles from an unknown class belong to the established class responsive to the recognition of the pattern by the data detected from the sample particles.

In another embodiment of this aspect of the present invention, a method detects and classifies biological particles of interest from a heterogeneous population of biological particles. This method includes moving particles, substantially one at a time, in a fluid flow stream. An incident beam of illuminaton is preferably provided and is directed at the particles in the flow stream. Light-related data associated with each moving particle, as it passes through the beam of illuminaton, is detected. A class of particles is established, with such particles having common characteristics based on the light data detected from such class of particles. Such light-related data is then stored. The method further includes separating the class into a plurality of subclasses, with each subclass having its light-related data stored separately. Such stored data is compared to light data detected from sample particles of an unknown class. Finally, the present method determines that particles from the unknown class belong to the established class as a result of matching respective light-related data and identifies the subclasses to which the unknown particles belong.

In accordance with the principles of the present invention, pattern recognition techniques are relied upon to improve the performance of particle classification using multiparameter flow cytometric data. The techniques described herein introduce "intelligent aids" in the system for automatic biological particle detection and classification. The pattern recognition approach generates an effective and efficient description of the particles, determines the feature distinctions among various types of cells and classifies the unknown cells based on the extracted features. Accordingly, there is significant utility in pattern recognition algorithms, which may process information more rapidly and accurately than other methods. These advantageous features facilitate the development of rapid, non-growth methodologies for biological particle detection and classification.

A deterministic pattern recognition approach for the detection of biological particles by flow cytometry techniques is a principle underprinting of the present invention. A new algorithm has been developed which defines detection regions in a multi-dimensional space using features commonly measured by flow cytometry apparatuses. For the detection of certain type of particles, such as bacteria, data from a pure specimen is collected as a training set. A principal component transformation of the training data set is performed to obtain the new uncorrelated features. A clustering transformation is then applied to compress the data into a more compact form. Lastly, a detection region is defined preferbly as a hypersophere with two standard deviations as the radius to include the tightened cluster. The region may then be used to differentiate particles of interest from background particles in unknown samples. In terms of signal-to-noise ratio, the present invention shows significant improvement as compared to those obtained by the conventional rectangular gating method.

The principal component method has also been applied to the study of classification of biological particles. Besides the principle component technique, other particle classification techniques fall within the purview of the present invention. For speed improvement, a technique based on the Bayes rule has been developed. For handling events with shared membership, a technique based on the cluster characteristics has been developed. For a nonparametric approach, a technique based on the k-nearest neighbor rule has been developed. There are advantages and unique features inherent in each of these computer-aided biological particle classification techniques. It is expected that the use of pattern recognition algorithms to detect, analyze and classify flow cytometric biological particle data intellegently shoud simplify and expedite biological particle anaysis.

BRIEF DESCRIPTION OF THE DRAWINGS

FIG. 10a represents the contour plot of the original data, whereas FIG. 10b represents the resultant cluster after applying the cluster-seeking algorithm.

DETAILED DESCRIPTION

Figure 1:
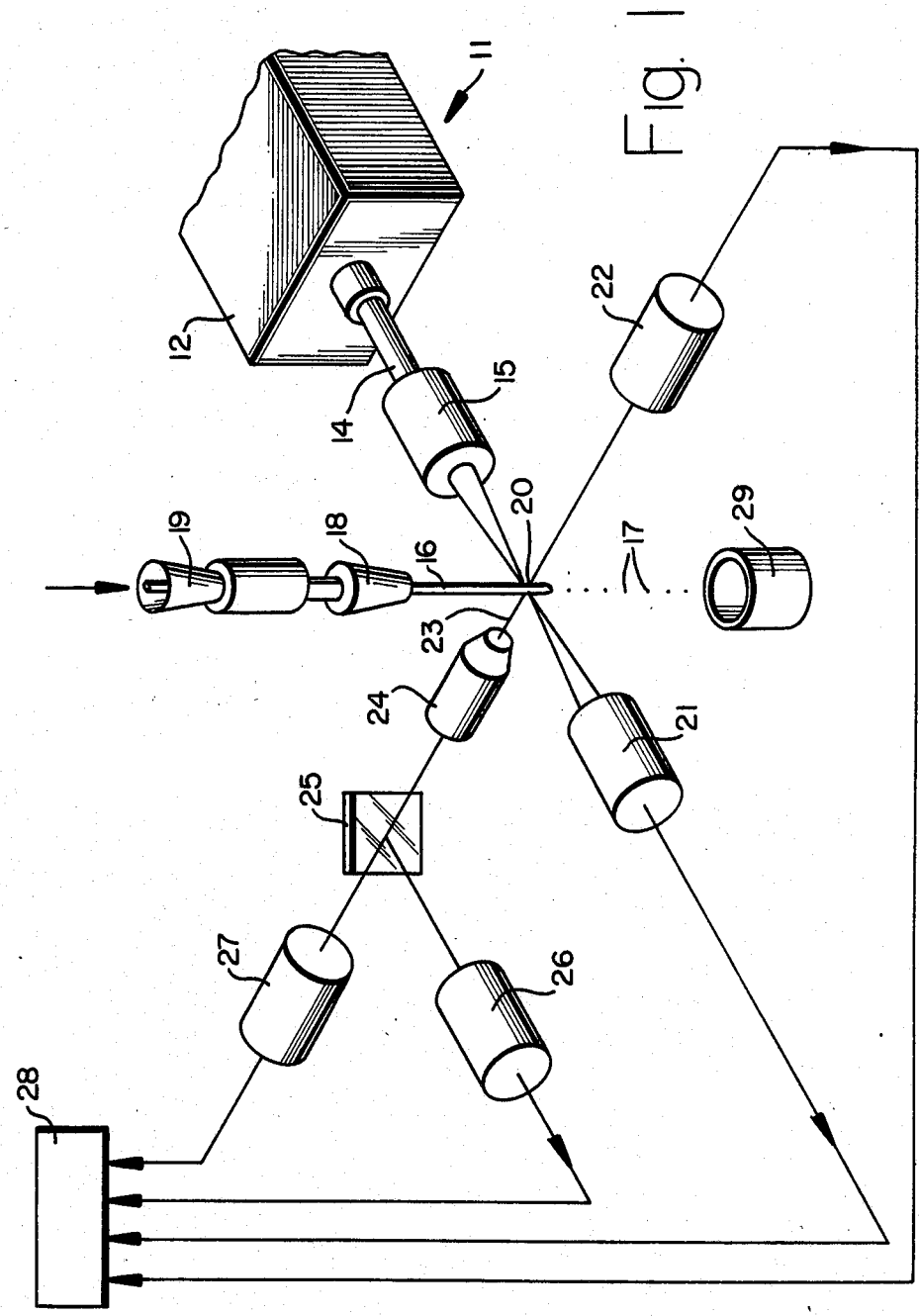
FIG. 1 is a schematic illustration of typical optical elements and light paths of a preferred flow cytometry apparatus for the detection and classification of biological particles of interest in accordance with the principles of the present invention.

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

Adverting to the drawings, and FIG. 1 in particular, the optical and particle flow elements of a typical flow cytometry apparatus 11 are illustrated. The optical and flow elements of FIG. 1 represent the major component of a preferred flow cytometry apparatus for moving particles, such as cells or the like, in a fluid flow stream, substantially one at a time, in order to assess those particles for specific characteristics thereof. For example, the elements of the device of FIG. 1 may be included in a FACS ™ fluorescence-activated cell sorter, manufactured and sold by the FACS Systems Division of Becton, Dickinson and Company, Sunnyvale, Calif. The FACS cell sorter analyzes and sorts cell populations on the basis of light scatter and fluorescence in a wide variety of research laboratory applications. In addition to the optical and flow elements to be described in more particular detail herein, and which may be embodied in an instrument such as the FACS cell sorter, other details of a cell sorting apparatus useful in conjunction with the present invention are described in U.S. Pat. No. 3,826,364 and the Scientific American publication referred to above. It is understood that the present invention is useful in many different types of flow cytometry or flow fluorometric apparatuses, whether measuring light scatter, particle volume, fluorescence, combinations of the foregoing or other optical, electrical or accoustical parameters for the identification, quantification or classification of cells or the like in a sample fluid medium.

As illustrated in FIG. 1 light energy is provided for the flow cytometry apparatus by a light source 12 such as a laser which provides a collimated beam of light at a singular wavelength or an arc lamp, such as a mercury or xenon arc lamp, which provides an incoherent or non-collimated beam of light comprising a broad spectrum of wavelengths.

Excitation energy is provided in flow cytometry apparatus 11 by a beam of light 14 produced by light source 12. Typically, the beam of illumination passes through focusing lens 15 which focuses the light beam at the liquid stream 16 containing the particles or cells 17 under investigation.

A nozzle 18, incorporated within the flow cytometry apparatus of the present invention, facilitates the flowing of particles or cells 17 within fluid stream 16. The utilization of a nozzle of this type is well-known and is described, for example, in U.S. Pat. No. 3,826,364. A sheath liquid 19 is normally utilized to ensheath particle stream 16 so as to produce a hydrodynamically focused fluid flow system. As each cell or particle passes through the focused light region 20, where light beam 14 intersects liquid stream 16, light scattered thereby may be detected by an appropriate photodetector 21. In the embodiment being described, photodetector 21 detects light scattered in a forward direction, typically at an angle between 0.5° and 10° with respect to the axis of the beam of light. At the same time, light scattered in an orthogonal direction from cells 17 passing through the light beam is detected by an appropriate photodetector 22.

Similarly, fluorescence, if emitted by particles energized by the illumination from the light source, may also be detected. Fluorescence emitted by autofluorescent particles or fluorescently labeled particles in fluid stream 16 is detected along fluorescence axis 23 which is typically at a right angle with respect to the axis of light beam 14. Fluorescence emitted by the flowing particles may pass through an appropriate filter 24 before it travels to a dichroic mirror 25. This dichroic mirror, well known to those versed in the art, permits certain wavelengths of light to pass through while reflecting other wavelengths. In this regard, fluorescence emitted from the particles at different wavelengths may be detected in fluorescence detectors 26 and 27.

Photodetectors 21 and 22 and fluorescence detectors 26 and 27 may be well-known photomultiplier tubes or similar devices which convert light signals into electrical impulses so that the light thereby detected may be associated with the fluorescently labeled cells and cells of a specific size flowing through the apparatus. The electrical signals from the photodetectors and fluorescence detectors are typically fed to the electronics 28 of the apparatus for purposes of display, storage or further processing so that one or more characteristics of the cells under analysis may be determined.

In the arrangement being described, light scatter and fluorescence may be detected simultaneously with respect to each particle through focused light region 20. Particles 17 in the liquid stream may be collected in an appropriate container 29, or, perhaps, may be sorted and collected in different containers if the flow cytometry apparatus employs a sorting capability.

Now that the major elements of a flow cytometry apparatus have been described, the pattern recognition techniques of the present invention will be more fully appreciated. The algorithms of the present invention which carry out and apply the pattern recognition techniques for biological particle classification will be understood to be included in the electronics 28 of the instant apparatus. For purposes of the ensuing discussion, pattern recognition techniques will be exemplified by reference to bacteria detection and classification. For example, the detection features of the present invention were tested with respect to bacteria in peripheral human blood. On the other hand, the classification of bacteria in human urine specimens was also studied with respect to the present invention. However, the principles of the present invention have wide applicability for the detection and classification of biological particles whether such particles be microorganisms in various biological fluids, or cellular analysis such as the identification and enumeration of various subclasses of leukocytes.

Data analysis for bacterial detection involves categorizing particles as members of one specific bacterial species to which they belong. Pattern recognition methods are uniquely suited to this type of study. In the pattern recognition approach, once a specific design method is selected, the cell classifier has to be trained to recognize particles from the class under consideration. This is the so-called supervised learning approach. The classifier is "taught" to detect cells through the procedure of learning the common characteristics from a set of representative particles in the class. This set of training patterns of known classification is an important element for this method. The training sets in the analysis are typically obtained by preparing samples with a high concentration (usually $10^6$ or $10^7$ particles per milliliter) of a known type of bacteria. Data files collected in the flow cytometry apparatus from the samples are referred to as calibration files. In the learning process, cell classifiers extracted a set of descripters for each type of bacteria from the calibration file and applied it to the unknown samples for bacteria detection.

Since particles may be described by numeric characterization of their properties, vectorial representation and decision-theoretic approach to classification logic are utilized for the present invention. A particle having measured values $x_1, x_2 \ldots x_n$ for n-features is represented by the vector $\bar{x}=(x_1,x_2 \ldots x_n)$ in n-dimensional space in which each coordinate axis is associated with a specific feature. Since the coordinate values are measurements, x is a random vector of observations. The vector space spanned by all possible random vectors constitutes the feature space or parameter space for the classification problem. Further, for each of the particle classes, a corresponding region is formed in this space. These classes are presumed collectively to account for all classification contingencies, and exclude the region for background particles which are not in these classes.

A key item in classification of particles is the development of decision functions to partition the parameter space into regions which contain the sample points of each class. Toward this goal, an algorithm, herein called the principal component method (PCM), was developed. The PCM involves a clustering transformation which is made on the measurement space in order to cluster the points representing elements of the class. Such a transformation minimizes the intraset distance between pattern points of the same class. Another significant step in developing decision functions is feature extraction which is the procedure of selecting the most effective features for discrimination purposes. Good features enhance within-class pattern similarity and between-class dissimilarity. Feature extraction consists of extracting a number of features, each of which is a linear combination of all of the initial measurements. This approach may be viewed as transforming the original measurement space to another representation space and finding the subspace for the class which best preserves the information available in the original space.

Clustering transformation is used to increase the similarity of patterns in the same class through a minimization of a metric between the points defining the class. The metric between two points is measured by the Euclidean distance. The more distant the patterns of different classes are from each other, the better chance of correct recognition of class membership. Physical closeness is judged on the distance between two pattern points. Thus, distance measures are the fundamental concept in processing pattern information.

The mean square intraset distance, denoted by $D^2$, for a class may then be expressed in terms of the variances associated with the components of the pattern vectors in the set. This distance measure is used in the study of clustering transformation and is expressed according to the following relationship:

$$D^2 = 2 \sum_{k=1}^{n} \sigma_k^2$$

where: $\sigma_k$ is the unbiased sample variance of the components along the $x_k$ direction Measurements of a pattern are represented by different coordinate axes, $x_k$, in the n-dimensional space. These parameters are not all equally important in defining the region in which same patterns belong. To compare two patterns feature by feature, measurements with least significance should be assigned least weights. Measurements which convey reliable discrimination information should be weighted heavily. The process of feature weighting may be realized through a linear transformation which will cluster the pattern points in the new space. It minimizes the intraset distance for some particular class in the hope of condensing that class and thus making the classification task easier.

Consider two vectors $\bar{a}'$ and $\bar{b}'$ in space S', which are transformed from vectors $\bar{a}$ and $\bar{b}$ in space S by a transformation matrix $\overline{W}$. They can be written as $\bar{a}' = \overline{W} \bar{a}$ and $$\bar{b}' = \overline{W} \bar{b}$$

where $$\overline{W} = \begin{bmatrix} w_{11} & w_{12} & \ldots & w_{1n} \\ w_{21} & w_{22} & \ldots & w_{2n} \\ \cdot & & & \cdot \\ \cdot & & & \cdot \\ \cdot & & & \cdot \\ w_{n1} & w_{n2} & \ldots & w_{nn} \end{bmatrix}$$

in which $w_{ij}$ are the weighting coefficients. $\overline{W}$ is the matrix which represents a general linear transformation. The weighting process that is of interest only involves the parameters of the main axes. When the linear transformation is performed with only scale-factor changes of the coordinates, W may be a diagonal matrix with only the elements on the main diagonal being nonzero. Since each element of the transformed vector is a linear combination of the elements of the original vector, the new components may be written as:

$$a'_k = w_{kk} a_k$$

and $$b'_k = w_{kk} b_k$$

Therefore, the Euclidean distance between $\bar{a}$ and $\bar{b}$ in the new space is represented by the intraset distance for pattern points according the the following relationship:

$$D^2 = 2 \sum_{k=1}^{n} (w_{kk} \sigma_k)^2.$$

In this equation, $w_{kk}$ is the only unknown and to avoid trivial solutions some additional constraint must be applied to the W matrix. The constraint considered is:

$$\prod_{k=1}^{n} w_{kk} = 1$$

The above relationship implies a constant volume weighting and is related to the norm of the parameter space. Using the Lagrange method, the minimization of $D^2$, subject to the foregoing restraint, results in the following relationship:

$$w_{kk} = \frac{1}{\sigma_k} \left( \prod_{j=1}^{n} \sigma_j \right)^{1/n}$$

which is inversely proportional to the standard deviation of the measurements. Those coordinates that have greater variances provide little in common over the patterns of the class; accordingly, the weight factors are small. Conversely, if the variance is small, its contribution to the clustering is large and is weighted heavily.

Since the feature-weighting coefficients, w determine the transformation matrix W under the constraint specified above, and if the pattern vectors are transformed from space S to S' by the transformation $$\overline{x'} = \overline{W} \overline{x}$$

the intraset distance between points in space S' is minimized. This is the so-called clustering transformation for the data points of a class.

Extraction of features from training patterns is a function of determining certain relatively invariant attributes of the pattern class. Prior to determining which components in the data have small or large variances, the data is preprocessed to construct new features that are uncorrelated, since some of the features chosen may be correlated (i.e., one measured parameter may depend upon some or all of the other variables). Some technique is required for extracting the uncorrelated features when the measurements are correlated in nature. The mathematical form of the function which measures the correlation among the variables in the covariance matrix, and satisfies the following relationship:

$$\overline{C} = \begin{bmatrix} \sigma_{11} & \sigma_{12} & \cdots & \sigma_{1n} \\ \sigma_{21} & \sigma_{22} & \cdots & \sigma_{2n} \\ \cdot & \cdot & \cdots & \cdot \\ \cdot & \cdot & \cdots & \cdot \\ \cdot & \cdot & \cdots & \cdot \\ \sigma_{n1} & \sigma_{n2} & & \sigma_{nn} \end{bmatrix}$$

For uncorrelated variates, the covariance matrix is a diagonal matrix; i.e., the off-diagonal elements are zero. It is known that in a similarity transformation (i.e., $\overline{C'} = \overline{A}\overline{C}\overline{A}^{-1}$) the matrix $\overline{C}$ will be diagonalized by matrix $\overline{A}$ if $\overline{A}$ is chosen as the modal matrix of $\overline{C}$. For a modal matrix, the columns of $\overline{A}^{-1}$ are the eigenvectors of $\overline{C}$, or, in other words, the rows of $\overline{A}$ are the eigenvectors of $\overline{C}^{-1}$. Therefore, a modal matrix $\overline{A}$ will transform the original measurements into a space in which the covariance matrix is diagonal and the new coordinates are uncorrelated.

Associated with the measurement space estabished by the clustering transformation $(\overline{x'} = \overline{W}\overline{x})$ is a covariance matrix $\overline{C}'$, which may be formed from the original covariance matrix $\overline{C}$ through the transform $\overline{C'} = \overline{W}\overline{C}\overline{W}^T$. The superscript T, attached to the vector means that such vector is the transpose of $\overline{W}$. Then, the covariance of the components may be decoupled in the space S' by finding $\overline{A}$, the transform that maintains the minimum intraset distance and diagonalizes the covariance matrix. This results in a new space, S'', in which the contribution of the various uncorrelated components to the clustering is evident.

Recapitulating, the principal component method is based on obtaining the optimal set of features which best describe the structure of the data set. By applyingg it to the representative sample (calibration file), the most informative descripters of the multi-dimensional cluster of bacteria may be selected and thus the detection and classification task made easier.

In applying the aforementioned technique for detection of bacteria, pure bacterial specimens are used as training sets for the calibration files, as described above. For such data, the sample mean and sample covariance matrix constitutes a compact description. The sample mean locates the center of gravity of the cluster and the sample covariance matrix tells how well the sample mean describes the data in terms of the amount of scatter that exists in various directions. A feature extraction transformation may be obtained by diagonalization of the covariance matrix of the original data. The resulting eigenvectors are the rows of the desired transformation matrix, and the corresponding eigenvalues are the variances of the new features, which are linear combinations of the original components.

As described above, the features having smaller variances are expected to be more important in discriminating bacteria from nonbacteria and should be weighted more heavily in arriving at detection and classification decisions. This feature weighting process is realized through the clustering transformation which minimizes the data intraset distance, i.e., the mean-square distance between data points. With this transformation, the data is compressed into a more compact form. Under the assumption that the points in the training set (calibration file) come from a single multivariate normal distribution, the classification region can be obtained by defining a hypersphere (i.e., a "sphere" in four or more dimensions) with two standard deviations as the radius to include this tightened cluster. Then in the new space, an unknown particle may be recognized as bacteria if its distance from the cluster center is less than the radius of the hypersphere. On the other hand, an unknown particle will be recognized as non-bacteria if its distance from the cluster center is greater than the radius of the hypersphere.

Application of the principal component method for detection of biological particles will now be discussed. The detection or classification of particles in flow cytometry is based upon the light scatter and light-fluorescence measurements, or ratios of these measurements. These parameters form an analytic tool to identify a cell as a member of a specific cell type. In bacterial detection or classification, the cells are typically various species of bacteria. There are only two practical ways of recording these data: as lists of numbers and using a pictorial representation. However, for separation of bacteria from background particles or identification of bacterial types, maximum discrimination may only be achieved if all parameters are used in the multiparameter data analysis. The measurements should be recorded and then processed by sophisticated algorithms. The data recorded numerically as lists of parameters for each particle measured by the system are called list mode data, and are mainly for off-line data processing. Once data are collected in list mode, they may be displayed in the form of one-dimensional, two-dimensional histograms scatter plots, contour plots, etc., with full resolution. This data may also be analyzed using various algorithms on an event-by-event basis.

Figure 2:
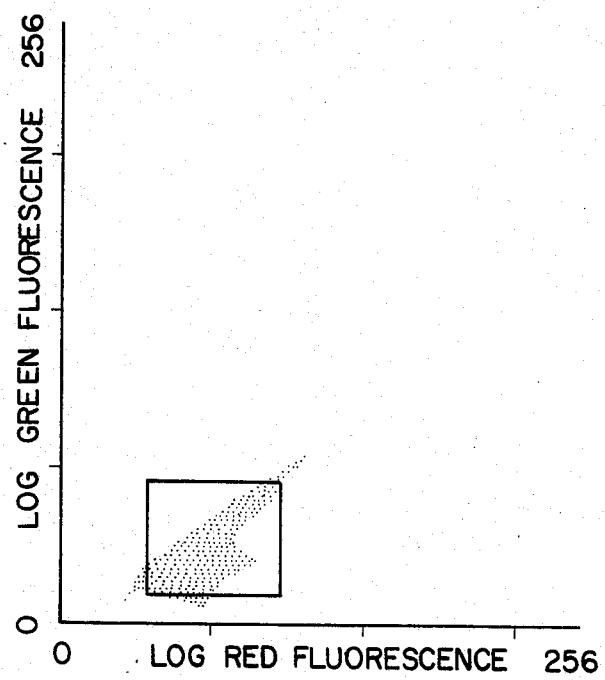
FIG. 2 is a two parameter (log red fluorescence and log green fluorescence) plot of *E. coli* and *P. mirabilis* calibration file in which the window represents the detection region determined by the rectangular gating method.

FIG. 2 illustrates an example of two types of bacteria in urine, E. coli and P. mirabilis, that are of interest. The detection of bacteria in urine involves a complex problem in which it is known only that one or two or three bacteria types is most likely to be encountered. It is important to know, for a patient urine sample, whether any of those bacteria is present, and how many. Typically, this problem has been handled by using a "universal" rectangular window to discriminate bacteria from background particles. In FIG. 2, the rectangle represents the two-dimensional universal window to establish the detection region determined by the conventional rectangular gating method. The window is typically made quite large to encompass the two training sets (calibration files) for the two species of bacteria. It can be seen that the excessive area occupied by the empty space in the window contributes error in signal detection.

Figure 3:
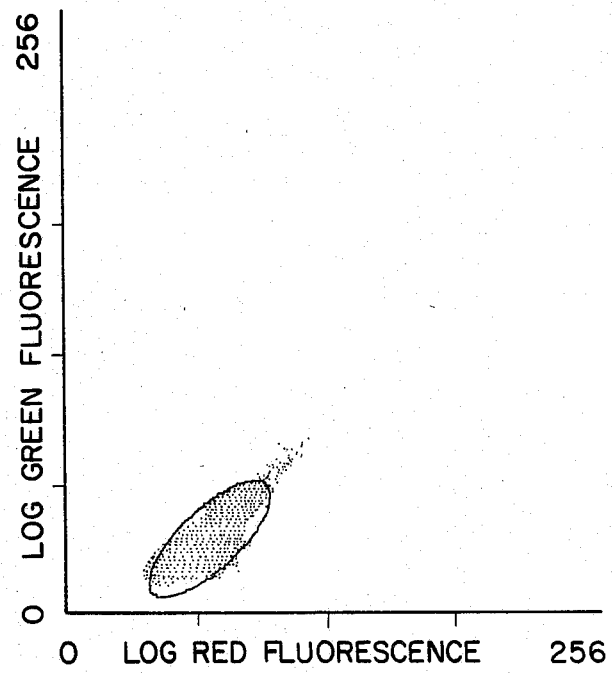
FIG. 3 is a two parameter (log red fluorescence and log green fluorescence) plot of *E. coli* and *P. mirabilis* calibration file in which the oval-shaped boundary represents the detection region determined by the principal component method.

In accordance with the present invention, the principal component method refines this discrimination of particles. FIG. 3 illustrates the two parameter plot of *E. coli* and *P. mirabilis* calibration file and the two-dimensional boundary calculated by the PCM algorithm. The oval-shaped boundary represents the detection region determined by the principal component method. It is clear that the region determined thereby fits the data more tightly than the universal window depicted in FIG. 2 which in turn reduces the errors in detection. The PCM method may be carried out in four dimensional logarithmic space with forward scatter, green fluorescence, red fluorescence and 90° scatter as the parameter axes. It has been found that the PCM technique provides a dramatic increase in signal/noise ratio, which indicates that the PCM approach is most useful even when the type of particles to be detected is not known, a priori.

Quantitative analysis of the principal component method is based on the information contained in the training set (calibration file). This numerically calculated information includes position, size, shape and distribution statistics of the cells contained in the sample. The PCM parameters that construct a better fitting surface for the isolated cell cluster in multidimensional space are directly derived from the mean and covariance of the multivariate sample distribution. In this approach, the PCM's use of all parameters simultaneously to obtain solutions to the complex structural problems provides an effective and efficient technique for discrimination.

Figure 4A:
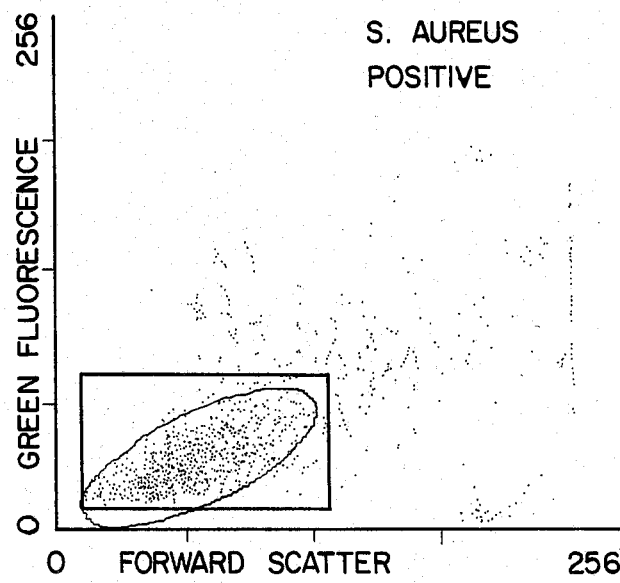
FIGS. 4A and 4B are comparisons of the linear and logarithmic principal component methods (PCM), respectively and the rectangular window gating method in the detection of *S. aureus* in blood wherein the oval and irregularly shaped regions were generated from PCM analysis using forward scatter and green fluorescence and the rectangle resulted from the window gating process.

In order to provide a more effective description of the bacteria and a more efficient classification region to discriminate the background particles, a modified principal component method may be employed. This modified approach requires preprocessing of the data to remove the skewness in the measurements. Then the characteristics and relations among the measurements are extracted for the representation of the cells of interest. Modification of the PCM is based upon a logarithmic transformation prior to the clustering transformation and feature extraction transformation so as to redistribute data approximately into a Gaussian distribution. In FIG. 4A, an overlay of the PCM boundary (oval shaped) is shown superimposed on the rectangular window generated by the window gating procedure. The oval boundary is a result of using linear PCM analysis.

Figure 4B:
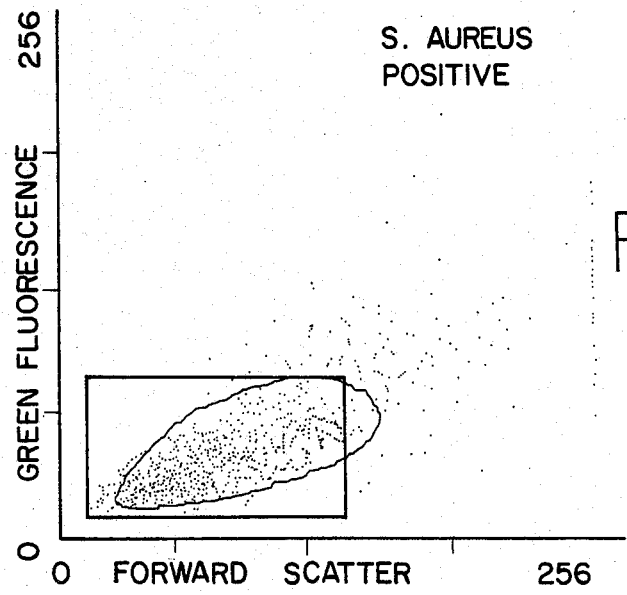

FIG. 4B illustrates the logarithmically modified principal component method compared to the universal rectangular window method. The data points in FIG. 4B represent the detection of *S. aureus* in blood. The irregularly shaped region was generated from PCM analysis of forward scatter and green fluorescence utilizing logarithmic transformation. The rectangle resulted from the universal window gating process. It can be seen that the modified PCM region fits the majority of events in the positive sample much better than the rectangular window and the linear PCM region as seen in FIG. 4A.

Figure 5:
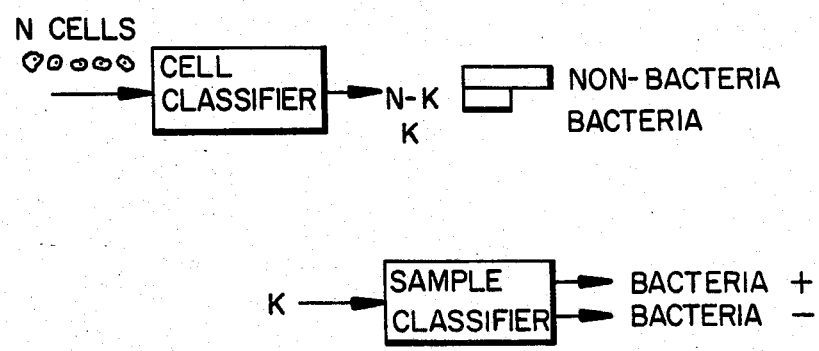
FIG. 5 is a schematic representation of a flow diagram for cell and specimen classification.

Classification of biological particles is a more refined technique once particles of interest have been detected. The foregoing description of the invention related generally to particle detection alone. FIG. 5 illustrates a cascaded model of cell and specimen classification. In the cell classification stage, K is the number of cells classified as bacteria. However, in practice, the value of K is corrupted by a certain number of background particles (noise) which also meet the pre-selected criteria for bacteria. The degree of corruption depends on how well the cell classifier performs. If the cell classifier were perfect in eliminating the contamination, any non-zero K value would sufficiently indicate the existence of bacteria. It is necessary, therefore, to select a non-zero detector threshold in the specimen classifier to test the hypothesis that the sample is bacteria positive. A sample is called positive if more bacteria than the threshold are detected in it and is called a negative if less than the threshold is detected in the sample. Adjusting the threshold value permits a tradeoff between the specimen false positive and false negative error rates. However, these error rates, in turn, depend upon the accuracy of the K values. Reducing the detection error in the cell classifier improves the accuracy of the K value, thereby reducing both error rates of the specimen classifier. With a reliable estimate of K, and the threshold adjusted to tradeoff false positive against false negative rates, one can attain the optimal classification performance.

Pattern recognition techniques for biological particle classification have been developed in accordance with the present invention. Algorithms capable of correct classification of biological particles were generated. By correct classification is meant that the algorithms are able to secure agreement between the computer analysis and the standard microbiology testing procedures which established the classification files for the specific particles. In particular, algorithms were developed to classify seven types of bacteria commonly encountered in practice: *Proteus mirabilis, Streptococcus faecalis, Staphylococcus saprophyticus, Klebsiella pneumoniae, Escherichia coli, Pseudomonas aeruginosa,* and Lactobacillus. It is understood, however, that algorithms for the detection and classification of other biological particles such as subclasses of lymphocytes may also be generated and fall within the purview of the present invention.

Classification of biological particles may be achieved by a number of different pattern recognition techniques including, but not limited to, the following: (1) the principal component method, (2) Bayes rule, (3) cluster statistics, and (4) the k-nearest neighbor rule.

As alluded to above, vectorial representation of biological particles maps the particles into points and particle classes into sets, in a space of limited dimensionality. For each particle class, a corresponding particle region is formed in the vectorial space. The particle regions and the region for background particles are assumed to be exhaustive and mutually exclusive. By quantitative characterization of particle data clusters, a measure of separation of the clusters is defined so that classification regions may be established. The basic measures that are relied upon for quantification are location, size and separation of data clusters. These properties help select analysis features which make different biological particle types look different and can identify which preparation method is the most efficient in discrimination.

In vectorial mapping of particles, a technique has been developed wherein four-dimensional data may be presented in two dimensions, utilizing a new two-dimensional feature space. The two new components of the feature space are derived from the measured parameters and account for most of the variation in the original data for all the data under consideration, so that effective dimensionality of the data may be reduced to two.

The present invention relies upon the Karhunen-Loeve (K-L) expansion theory which facilitates the technique for feature selection. Feature selection procedure is related to the performance of pattern recognition systems. Its function is to extract from the available data those features that appear most significant for classification purposes. The K-L expansion is well-known in communication theory and has been described by Fukunaga in "Introduction to Statistical Pattern Recognition," Academic Press, New York, 1972. This K-L expansion is based upon an eigenvector analysis of the sample covariant matrix associated with the input data. The results of this analysis are used to linearly transform the representation vectors for the points in all clusters into a new coordinate system in which the coordinate variables are mutually uncorrelated, and wherein the information from the original data distribution is concentrated in the first few axes of the new coordinate system. In this way, it is possible to approximate the representation vector with least mean square error by a new feature vector of reduced dimension. It is this combination of feature selection and reduction which make the K-L expansion a powerful general approach in pattern recognition problems.

One technique for displaying four-dimensional data in two-dimensional space, in accordance with a K-L expansion algorithm, is performed as follows:

(1) concatenate the data files of the training sets for all classes of bacteria of interest into one calibration file;
(2) calculate the mean and covariance matrix of this calibration file, in accordance with the above procedures;
(3) calculate the eigenvectors and eigenvalues for the covariant matrix;
(4) choose the two eigenvectors that correspond to the two largest eigenvalues of the covariance matrix which will form the basis for the new space;
(5) form a two by four transform matrix, $\overline{W}$, by using the eigenvectors chosen in step 4 as the rows of the $\overline{W}$ matrix; and
(6) compute the new data vector, $\overline{x}'$, using the relation $\overline{x}' = \overline{W}\overline{x}$ and display the new events in the new space.

The $\overline{x}'$ vectors are now the two-dimensional representation that minimizes the approximation error. Therefore, the number of features needed to describe the data has been effectively reduced. Actually, if all four new features were selected there would be no net reduction in features and the new data points would represent the old points after a coordinate rotation.

It is understood, for purposes of the present description, that the four-dimensional data for each particle of interest relates to forward scatter, 90° scatter, green fluorescence and red fluorescence as detected by the flow cytometry apparatus.

Figure 6:
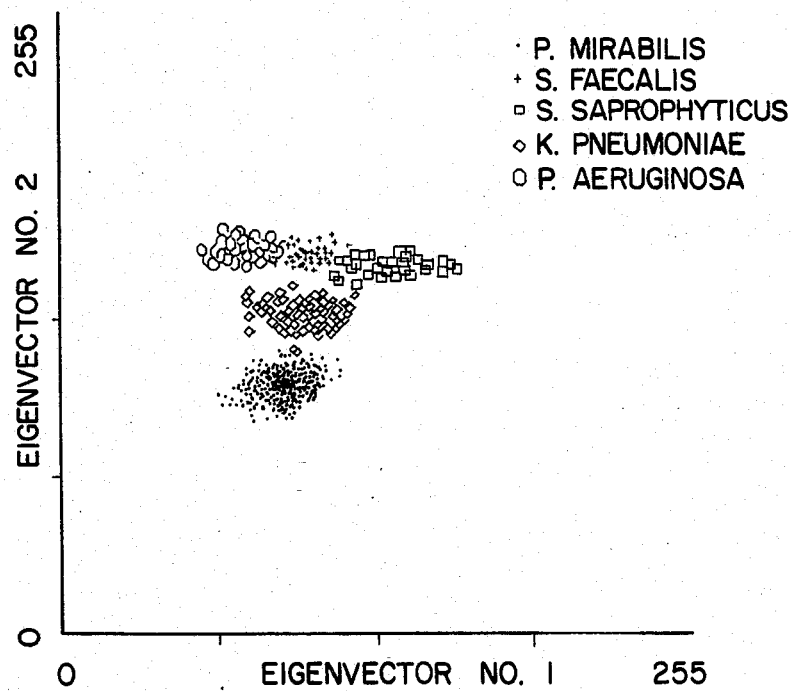
FIG. 6 is a scatter diagram of five types of bacteria in the space of the two dominant eigenvectors of the Karhunen-Loeve expansion.

FIG. 6 illustrates the results of analysis of five types of bacteria in urine: E. coli, P. mirabilis, S. saprophyticus, P. aeruginosa and Lactobacillus. The eigenvectors were extracted from the data set which contained all five types of bacteria, and ordered from highest to lowest in terms of their eigenvalues. The percent of variance preserved in the first two components was 93.5%. Since these are linear combinations of the original variables, it is expected that this plot should contain more information about the data structure than any simple two-variable plot, although it may be difficult to assign scientific meaning to the linear combinations. While different class members are represented by different types of markers in FIG. 6, it remains quite difficult to visualize the actual space for each individual class and the amount of shared space between classes. A plot of just the boundaries (or the classification regions) of the classes would be sufficient to show where the classes are and how much space each of them occupies. Of the four different classifications strategies listed above, the principal component method is most appropriate in defining the boundary of the individual classes.

In its application to the bacterial detection problem, the principal component method successfully distinguishes bacteria from background particles. PCM explicitly utilizes the structure of the particles to delimit a boundary between signal and noise as described above. An experimentally determined cluster may be encoded by a set of numbers which include two transformations, namely, feature extraction and clustering, and a center and radius in the transformed space. These numbers may be considered as elements of a specific feature set of the cluster. If it takes such a numerical form to characterize one class of bacteria, c sets of numbers should be sufficient to define the c classes that are under consideration. These sets of features essentially demarcate c classification regions in the measurement space. However, in this case, there exists the unoccupied space outside the union of the c classification regions, which is purposely designated for background particles.

The PCM method requires different training sets (calibration files) for different groups of bacteria which are to be classified. When all the training sets are processed to obtain the set of features, the multidimensional parameter space is partitioned into regions corresponding to different bacterial classes. These regions collectively account for the bacteria under consideration and exclude background particles. The classifier may be realized by testing if an input particles falls in any one of the c classification regions and assigning it to the class where the data vector lies, or assigning it as a background particles if it does not belong to any of the c classes.

Based on this approach, it is desirable to have the regions of the bacterial classes correspond to compact and well-separated clusters. However, the regions generated by different bacteria types overlap to various degrees. How to classify events falling in the overlapped regions must be resolved. Some additional decision-making processes have to be implemented in the classifier to handle such situations.

An intuitive solution is to adopt the concept of the nearest neighbor rule in pattern recognition which assigns a pattern of unknown classification to the class of its nearest neighbor. The event should be included in the class whose center is the closest. To define the idea of "closeness," it is necessary to first define a measure of similarity which will establish a rule for assigning patterns to the domain of a particular cluster center. In the nearest neighbor approach, the Euclidean distance has been generally considered. However, if one wishes to assess how far removed from the mean vector an individual particles is, one should not simply compute the Euclidean distance. This is because the values for the different components may not be independent of each other, but may show a covariance. The mutual correlation among the variables forming the cluster should be considered. A measure known as the Mahalanobis distance accomplishes this.

The Mahalanobis distance is a probability measure that represents the effective separation between two points after adjustment for the internal covariance of the parameters, and is defined as:

$$D_M = \bar{\iota}^T \bar{C}^{-1} \bar{\iota}$$

Here, $\bar{\iota}^T$ is a row vector of differences between a cluster center and an individual particle; $\iota$ is the corresponding column vector. $\bar{C}^{-1}$ is the inverse of the variance-covariance matrix. Conceptually, this determines finding which cell type the set of features of the event most resembles. The shorter the distance between the event and a cluster center, the more likely the unknown cell belongs to that class; and the longer the distance, the less likely the unknown cell belongs to that class.

Figure 7:
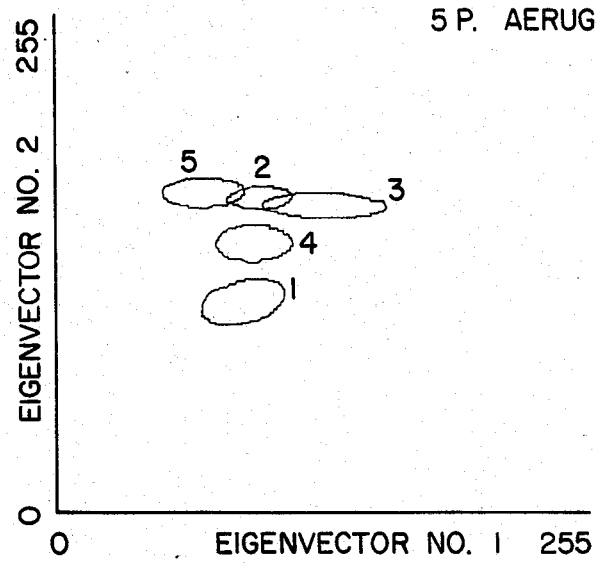
FIG. 7 is a graphic representation of cluster boundaries which have been determined by the principal component method (PCM) of the five types of bacteria in the space of the two dominat eigenvectors of the Karhunen-Loeve expansion.

Application of the PCM classification technique is illustrated in FIG. 7. Cluster boundaries which have been determined by PCM are delineated relating to the five types of bacteria in the space of the two dominant eigenvectors of the K-L expansion.

Figure 8:
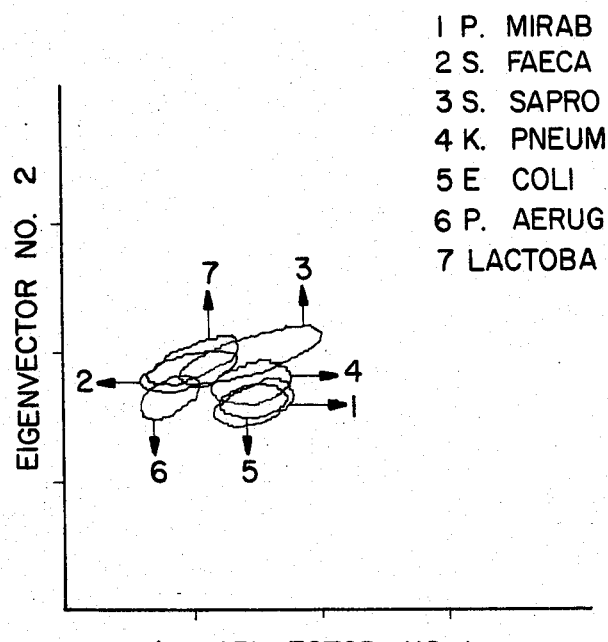
FIG. 8 is a graphic illustration of the classification boundaries of seven types of bacteria in the space of the two dominant eigenvectors of the Karhunen-Loeve expansion wherein the boundaries have been determined by the principal component method (PCM) employing data projected from the four-dimensional feafture space onto this two-dimensional eigenspace.

The *P. aeruginosa*, *S. faecalis* and *S. saprophyticus* classes, which are almost indistinguishable in FIG. 6, are clearly presented in FIG. 7. While the overlap between *S. faecalis* and *S. saprophyticus* may still be observed, the separation between *P. mirabilis* and *K. penumoniae* is significantly increased. Similarly, FIG. 8 illustrates the two-dimensional classification regions computed for seven types of bacteria: *P. mirabilis, S. faecalis, S. saprophyticus, K. pneumoniae, E. coli, P. aeruginosa* and Lactobacillus. The plot of FIG. 8 represents the space of the two dominant eigenvectors of the Karhunen-Loeve expansion. The boundaries have been determined by the principal component method employing data projected from the four-dimensional feature space onto this two-dimensional eigenspace. It is clear that class 1 (*P. mirabilis*) and class 5 (*E. coli*) have a large amount of overlap. There is some overlap of *S. faecalis* and lactobacillus, as well as interaction with *S. saprophyticus*. Although the extent of overlap was reduced in four-dimensional space, it is not surprising to see that some of the particles in the *P. mirabilis* specimen were assigned into the *E. coli* class by the PCM classifier, as shown in the following table:

| Class # | Class Name | Event Count | Confidence Value % |
|---|---|---|---|
| 1 | P. mirabilis | 822 | 85.71 |
| 2 | S. faecalis | 23 | 2.40 |
| 3 | S. saprophyticus | 0 | 0.00 |
| 4 | K. pneumoniae | 14 | 1.46 |
| 5 | E. coli | 100 | 10.43 |
| 6 | P. aeruginosa | 0 | 0.00 |
| 7 | Lactobacillus | 0 | 0.00 |
| | Background | 41/1000 | |

However, the sample was correctly classified because it contained significantly more cells labeled *P. mirabilis*.

Assuming normal data statistics, classification of biological particles, such as bacteria, may be achieved by application of the Bayes rule. According to the Bayes rule approach, statistical decision theory is relied upon to perform the classification. It partitions the feature space into c mutually exclusive and exhaustive regions $(R_1, R_2, \ldots R_c)$, corresponding to c bacterial types. Classification then consists in assigning a cell to the ith class if its parameters give the largest probability in the associated region, $R_i$. The use of probabilistic concepts is motivated by several considerations. First, they provide a tool for expressing the consequences of measurement variability that is unavoidable in data colllection. Second, they allow for quantitative measures of correlations between features. Finally, the statistical point of view acknowledges that there is an inherent ambiguity (i.e., shared memberships) attached to the discrimination process which makes error-free categorization unattainable. Bayesian decision strategy as relied upon herein is a suitable statistical approach because by design it minimizes the penalties for making errors.

The Bayes classifier favors assignment of an event, x, to the most likely source and maximizes the average success rate over the c classes. Its strategy is equivalent to a sequence of $c(c-1)/2$ pairwise comparisons, each resulting in elimination of the class corresponding to the smaller probability. At each step, the feature space is partitioned into two regions according to the sign of $d_{ij} = D_i(x) - D_j(x)$ where $i,j = 1, 2 \ldots c$, and $D_i$ and $D_j$ are the decision functions of class i and j, respectively. The region of positive sign is associated with class i and region of negative sign with class j. They are separated by a decision boundary on which $d_{ij}$ vanishes. The classification of class i is simply the common portion of all positive regions associated with class i. Its boundary consists of all points within pairwise decision boundaries which are not in any negative regions.

Figure 9:
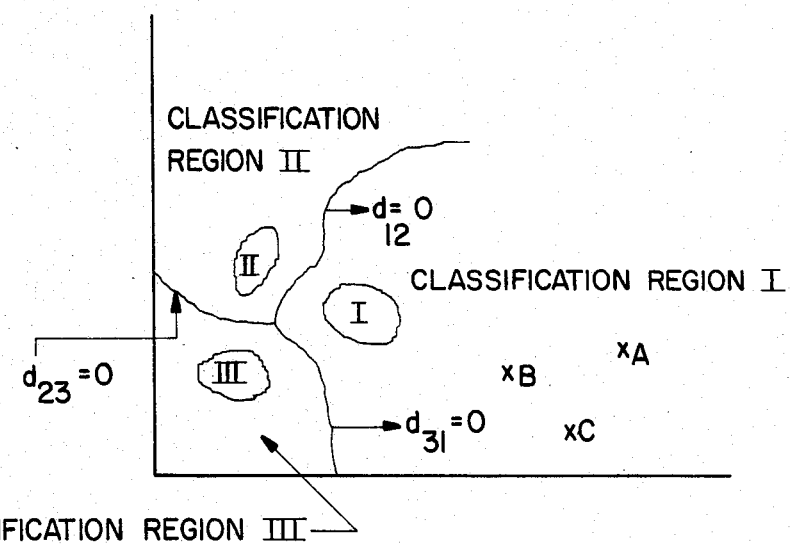
FIG. 9 is a graphic illustraton of three classes of particles and their corresponding classification regions determined by the Bayesian decision boundaries.

Implementation of a Bayes classifier for biological particles based on statistical decision functions consists of: first, evaluating the c function values for an input vector, x; second, selecting the largest one; and finally, assigning the unknown input particle to the corresponding class. An illustration of the Bayes rule approach is seen in FIG. 9. Three cell classes have been separated in the two-parameter space of FIG. 9. The region corresponding to class I consists of the area determined by the negative side of curve $d_{12} = 0$ and the positive side of curve $d_{31} = 0$. This area is indicated by "classification region I" in the figure. It is apparent that, although class I occupies a relatively small area, the actual classification region where a particle would be assigned to this class if very large in extent. Similar comments hold for the other two classes. The three points marked by A, B and C, shown clearly in the figure as background particles will be classified erroneously by the Bayes classifier as class I particles. This is one drawback in the Bayes classifier since it lacks the ability to handle ambiguous situations (e.g., when the probability of an event being in any of the classes is extremely small) in the decision making process. A remedy to this problem is to preprocess the features of an event to eliminate any obvious outliers.

Another approach to classify biological particles by pattern recognition techniques is the cluster feature technique. The previously described classification techniques concentrated on an event-by-event analysis. However, there may be enough numerical data information in measures of the group of events as a whole to determine if the biological particle is present. When substantiation of differences between two cell populations provides the diagnostic clue, it is usually not necessary that every single cell be properly classified; it is necessary merely to prove the significance of a difference between two classes. If the distinction is good enough to classify clusters without error, the difficulty of overlapped regions may be eliminated and the problem of particles with shared membership may be neglected.

The fundamental aspect for cluster classification is that the group of particles being considered as a cluster is assumed to be taken from a single bacterial population. This means that the data are expected to be representative of just one class of bacteria. Therefore, the initial step in cluster analysis, common to all bacterial data processing techniques, is to obtain a clear classification file. Rectangular gating methods are not good enough, since the structural features are very sensitive to particles outside the cluster. Accordingly, a cluster seeking algorithm was developed, in accordance with the present invention, whose goal was to retain the "natural" grouping in the data and effectively eliminate those outlying events.

A time efficient scheme has been developed in accordance with the present invention based upon the fact that, in flow cytometric data for biological particles, a cluster always exists. This observation is prompted by the fact that bacterial data usually exhibit a unimodal structure. Although the bacteria in the cluster may be either pathogenic or non-pathogenic, they each form a cluster in the parameter space. If there are not enough events in the cluster, the fluid sample is not considered clinically important. Based on these assumptions, utilizing a histogram for data representation becomes useful. The histogram maps the points in the cluster into a new form, characterized by large numbers on the frequency axis, and the remaining points to the surrounding area with small values for frequency counts. Because of these distinct value differences in the new format, the cluster may be identified more easily. The main idea here is to look for a central peak surrounded by a valley in the new $(d+1)$-dimensional space. The events forming the peak are constituents of the cluster in the original space and other events are considered noise.

The method for extracting a cluster includes applying a threshold to the histogram of the data. This involves choosing a level, T, such that all frequency counts greater than T are mapped into the cluster while all other frequency counts are mapped into the background. Since generating multi-dimensional histograms is impractical, the most informative and efficient approach is to form a two-parameter histogram. It is similar to a two-dimensional image, and the values of the frequency count are equivalent t the gray levels. The algorithm developed hereunder computes the histogram for two selected parameters, detects a peak, calculates a threshold, identifies the part of the histogram in which a cluster is located, and extracts the events which constitute the cluster from the original data.

The preferred algorithm involves constructing a two-dimensional histogram from two of the four measure parameters, which is of a lower resolution than the maximum possible resolution existing in the original measurements. The choice of a lower resolution would preserve the important features of the original cluster, but would reduce the computational and memory requirements imposed on subsequent steps. At lower resolutions, small clusters that are in proximity to a large one may be undetectable. By using a peak detector over the two-dimensional histogram, the interesting region may be discovered, and only that region needs to be retained for further analysis. The main task here is to find the part of the "picture" that differs significantly from the background. In other words, the boundary around the peak which delineates the cluster needs to be defined. Once the threshold is determined, the outline of a cluster may be produced by marking regions containing threshold transitions. The step of finding the outline of the region is important for the purpose of identifying particles in the cluster from the original data set. With the ability to retrieve, from the original data, those events which form the cluster, the algorithm may achieve maximum sensitivity in cluster characterization by using the remaining two-parameters.

Figure 10A:
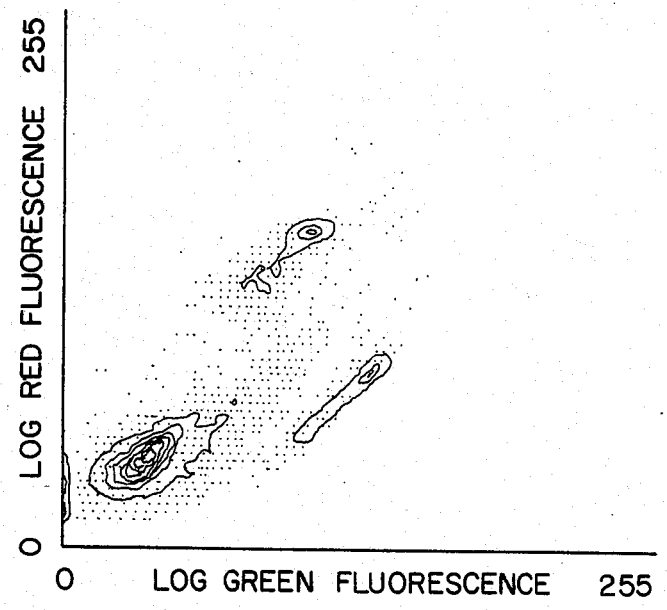
FIGS. 10a and 10b are graphic illustrations of the cluster determination by thresholding wherein the cluster-seeking algorithm was applied to extract the major portion of a cluster from noise-contaminated data.
Figure 10B:
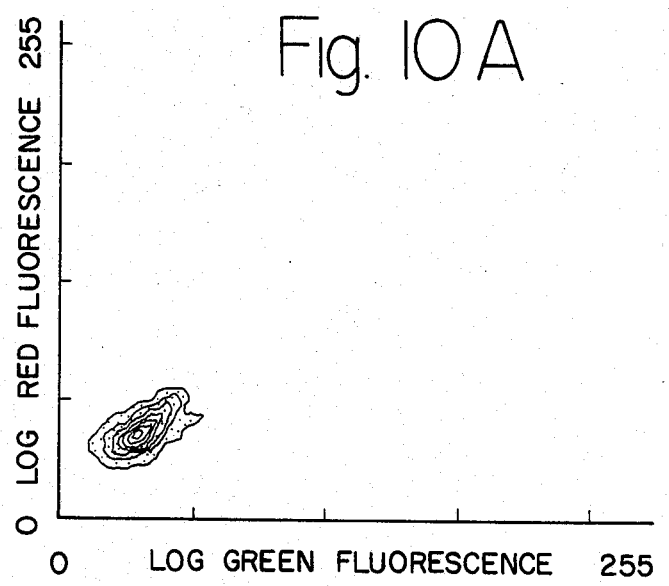

FIG. 10$b$ shows the resultant clusters after applying the cluster seeking algorithm on the original data sets, illustrated in FIG. 10$a$. Clearly, several insignificant background clusters are eliminated and only the dominant clusters are retained.

In cluster analysis for bacterial classification, it is desirable to prove the significance of a difference between two classes. This is based on using statistical tests which are highly sensitive in terms of assessing the significance of differences observed. Various test statistics commonly used in multivariate analysis may be employed to assess the significance of those differences. For example, multivariate analysis may be employed to determine the significance of a difference between the mean vectors of two multivariate distributions. Further, another test may be employed to detect small differences in the variance-covariance structure of two samples.

In the previous sections, the supervised learning was treated under the assumption that the underlying density functions were approximately normal. Although this assumption seems reasonable, due to the intense unimodal clumping of the bacterial data and the satisfactory results, the common parametric forms rarely make an exact fit with the densities. Accordingly, nonparametric methods of pattern recognition are also within the purview of the present invention. One such nonparametric pattern recognition technique is the nearest neighbor rule, which by-passes probability estimation and goes directly to decision functions.

Roughly speaking, nearest neighbor rules exchange the need to know the underlying distributions for that of knowing a large number of patterns. The basic ideas behind this approach are that points which fall close together in feature space are likely to either to belong to the same class or to have about the same probabilities of being in their respective classes. The first of these ideas gives rise to the formulation of the single nearest neighbor rule (1-NNR), while the second provides the formulation of the k-nearest neighbor rule (k-NNR).

The implementation of the k-NN rule in a classifier is not as complicated as the previously described techniques. For each unknown event, the nearest neighbor rule calculates the distances between all pairs of points and sorts the values into ascending order. The closest k points and their memberships are then determined. Among these k points, the class which contains the majority of events is selected for the unknown particle. However, if the total number of events in the selected class does not exceed a threshold value, L, the unknown particles are classified as background particles. The threshold value safeguards the classifier against excessive classification error by resorting to such rejection option.

As a nonparametric classification algorithm, k-NN rule relies on similiarity or proximity in feature space rather than maximum likelihood as the basis for class membership. It assigns the unknown particle to the class by examining a similarity measure defined for all pairs of objects in all the classes. The similarity measure preferably used is the Euclidean distance.

The theoretical justification supporting the k-NN rule procedure is based on infinite sample size, a condition which rarely occurs in practice. Accordingly, the k-NN rule should be used only when a very large training set (calibration file) is available.

Thus, the present invention provides a flow cytometry apparatus and method for the detection and classification of biological particles. In accordance with the principles of the present invention, pattern recognition techniques have been developed which significantly improve the performance of biological particle detection and classification. It has been demonstrated herein that flow cytometric classification of particles is qualitatively enhanced from an analysis which simultaneously uses all the measured features of the particles under investigation.

What is claimed is:

1. A flow cytometry apparatus for the detection of biological particles of interest from a sample of unknown biological particles comprising:
   means for moving particles from a sample of biological particles of an unknown class, substantially one at a time, in a fluid flow stream;
   means for providing an incident beam of illumination directed at the particles in said flow stream;
   means for detecting light-related data associated with each moving particle as the particle passes through said beam of illumination;
   means for storing data representing a known class of particles having common characteristics based on light data collected from such known class of particles;
   means for applying such stored data to light data detected from sample particles of said unknown class in order to match patterns between the data of the known and unknown particles; and
   means for recognizing that particles from said unknown class belong to said known class as a result of matching patterns of respective light-related data.

2. The apparatus of claim 1 wherein said means for detecting light-related data includes means for detecting a plurality of different light signals.

3. The apparatus of claim 2 wherein said means for detecting includes means for detecting light scattered by the particles and fluorescence emitted from the particles passing through said beam of illumination.

4. The apparatus of claim 3 wherein said means for detecting detects said light scatter and fluorescence signals simultaneously.

5. The apparatus of claim 3 wherein said means for detecting includes means for detecting light scattered in at least two different directions and for detecting fluorescence emitted by particles at a minimum of two different wavelengths.

6. The apparatus of claim 1 wherein said means for storing includes an electrical circuit with memory means, said circuit including means for converting light signals into electrical signals.

7. The apparatus of claim 1 wherein said means for applying data to match patterns includes decision function means operative to partition a space for measuring light data into a region which contains the sample particle data belonging to said known class.

8. The apparatus of claim 7 wherein said decision function means includes means for transforming the data of said measurement space in order to cluster the sample particle data into data points representing elements of said known class.

9. The apparatus of claim 8 wherein said clustering transformation means is capable of transforming vectors relating to pattern data of said measurement space to a new space according to the following relationship:

$$\overline{x}' = \overline{W}\overline{x}$$

wherein:
  $\overline{x}$ is the original vector of the measurement space
  $\overline{x}'$ is the transformed vector
  $\overline{W}$ is the transformation matrix comprised of variable weighting coefficients, $w_{ij}$.

10. The apparatus of claim 9 wherein said clustering transformation means is capable of minimizing the intraset distance between data points of the known class.

11. The apparatus of claim 10 wherein the transformation means is capable of relying upon the following relationship in minimizing intraset distance for data points in the transformed space:

$$D^2 = 2 \sum_{k=1}^{n} (w_{kk} \sigma_k)^2$$

where:
  $D^2$ is the mean square intraset distance between two points in a multidimensional space
  $\sigma_k$ is the unbiased sample variance of the components along the x direction $w_{kk}$ is the variable weighting factor, and for minimizing $D^2$, $$w_{kk} = \frac{1}{\sigma_k} \left( \prod_{j=1}^{n} \sigma_j \right)^{1/n}.$$

12. The apparatus of claim 7 wherein in said decision function means further includes means for extracting features from said stored data of the known particles for the discrimination of data related to said unknown particles.

13. The apparatus of claim 12 wherein said means for extracting is capable of extracting a plurality of features of said stored data, each feature being a linear combination of all of the original stored data measurements.

14. The apparatus of claim 13 wherein said means for extracting is capable of extracting uncorrelated features of said stored data when the measurements of said features are correlated in nature, whereby the mathematical form of the function which measures the correlation among the features is a covariance matrix.

15. The apparatus of claim 14 wherein said means for extracting is capable of transforming the stored data of the original measurement space to another representation space and of determining a subspace for the class which substantially preserves the data available in the original measurement space, according the the following mathematical relationship:

$$\overline{C}' = \overline{W}\overline{C}\overline{W}^T$$

where, $\overline{C}'$ is the transformed covariance matrix
$\overline{C}$ is the original covariance matrix
$\overline{W}$ is the transformation matrix comprised of variable weighing coefficients, $w_{ij}$
$\overline{W}^T$ is the transposed form of the transformation matrix, $\overline{W}$.

16. The apparatus of claim 15 wherein said means for extracting is capable of decoupling the covariance of the component features by relying on a modal matrix which transforms the original measurement space into a new space wherein the covariance matrix is diagonal and the coordinates of the new space are uncorrelated.

17. The apparatus of claim 16 wherein said means for recognizing includes means for defining a region for said known class as a hypersphere with a specified radius in the new space, said recognizing means further capable of designating that an unknown particle belongs to said known class if its distance from the cluster center is less than the radius of said hypersphere.

18. An apparatus for the detection of particles in a sample comprising:
sensing means, including a sensing zone, for sensing characteristic features of particles;
means for moving particles of an unknown class, substantially one at a time, in a fluid flow stream through said sensing zone;
means for detecting data associated with the characteristic features of each moving particle as the particle passes through said sensing zone;
means for storing data from a known class of particles having common characteristics in accordance with a pattern of data collected from such known class of particles; and
means for recognizing that sample particles from said unknown class belong to said known class responsive to the recognition of said pattern by data detected from said sample particles.

19. A flow cytometry apparatus for the detection of biological particles of interest from a heterogeneous population of biological particles comprising:
means for moving particles, substantially one at a time, in a liquid flow stream;
means for providing an incident beam of illumination directed at the particles in said flow stream;
means for simultaneously detecting light scattered by and fluorescence emitted from each moving particle as the particle passes through said beam of illumination;
means for storing data representing a known class of particles having common characteristics based on scattered light and fluorescence data collected from such known class of particles;
means for transforming light data detected from sample particles of an unknown class in order to cluster the data points so transformed;
means for extracting features from said stored data for the discrimination of data related to said unknown particles; and
means associated with said transforming and said extracting means for determining that particles from said unknown class belong to said known class as a result of matching patterns of respective light-related data.

20. A flow cytometry apparatus for the detection and classification of biological particles of interest from a sample of an unknown class of biological particles comprising:
means for moving particles from a sample of unknown biological particles, substantially one at a time, in a fluid flow stream;
means for providing an incident beam of illumination directed at the particles in said flow stream;
means for detecting light-related data associated with each moving particle as the particle passes through said beam of illumination;
means for storing data representing a known class of particles having common characteristics based on said light data collected from such known class of particles;
means for separating data from said known class into a plurality of subclasses thereof, each subclass having its light-related data stored separately;
means for applying such stored data to light data detected from sample particles of said unknown class in order to match patterns between the data of the known and unknown particles; and
means for recognizing that particles from said unknown class belong to said known class as a result of matching patterns of respective light-related data and for identifying the subclasses to which the unknown particles belong.

21. The apparatus of claim 20 wherein said means for detecting is capable of numerically characterizing said subclasses by vectorial representation in a space.

22. The apparatus of claim 21 wherein said means for recognizing is capable of mapping particles into points and particle subclasses into clusters in a space of limited dimensionality.

23. The apparatus of claim 22 wherein said means for recognizing performs said mapping by providing a two-dimensional presentation of four-dimensional data.

24. The apparatus of claim 23 wherein said means for recognizing is capable of extracting from said stored four-dimensional data those features that are most significant for classification purposes, and to linearly transform the representation vectors of the original clusters into a new coordinate system wherein the coordinate variables are mutually uncorrelated and the data from the original clusters are concentrated in the first few axes of the new coordinate system.

25. The apparatus of claim 24 wherein said means for recognizing extracts said features by performing an eigenvector analysis of a covariance matrix associated with data of said original clusters and utilizing the two largest eigenvalues of the covariance matrix as the basis for the new two-dimensional space.

26. The apparatus of claim 20 wherein said means for recognizing is capable of identifying subclasses by utilization of statistical decision means.

27. The apparatus of claim 26 wherein said statistical decision means is capable of partitioning the original data storage region into a plurality of mutually exclusive and exhaustive subregions corresponding to the number of subclasses and assigning a particle to one of said subclasses if its light-related data give the largest probability in the associated subregion.

28. The apparatus of claim 20 wherein said means for recognizing is capable of identifying subclasses by distinguishing particles of interest from background particles by reliance on the data representing structure of the particles to delimit the boundary between signal and noise.

29. The apparatus of claim 28 wherein means is included to cluster data representing subclasses of particles by encoding a set of numbers for each subclass of particles produced by two mathematical transformations, said sets each being further functionally represented by a center and a radius in the transformed space, wherein an unknown particle is identified as belonging to a known subclass if its data vector falls into the specific encoded set of numbers.

30. The apparatus of claim 20 wherein said means for recognizing is capable of identifying subclasses by distinguishing clusters of particles of interest from other clusters or from background particles by reliance on the data representing structure of the particles to delimit the boundary between clusters.

31. The apparatus of claim 30 wherein means is included to distinguish clusters by utilizing a histogram for data representation wherein points of data in the histogram are mapped into a new form represented by large numbers of the frequency axis thereof, the remaining points being assigned to surrounding area with small values for frequency counts.

32. The apparatus of claim 31 wherein said histogram is capable of identifying a cluster of interest in response to the application of a frequency threshold to the histogram data such that all frequency counts greater than the threshold are mapped into the cluster and all other frequency counts are mapped into a background region.

33. The apparatus of claim 20 wherein said means for recognizing is capable of identifying subclasses by examining a similarity measure defined for all pairs of points in all the subclasses.

34. The apparatus of claim 30 wherein said similarity measure is a Euclidean distance between all pairs of points.

35. The apparatus of claim 34 wherein said means for recognizing calculates the distance between all pairs of data points and sorts the calculated values into ascending order to determine the nearest neighbors of all points, unknown particles being assigned to the subclass in which a majority of neighboring points occurs.

36. The apparatus of claim 35 wherein a threshold number of points are stored in said means for storing so that said threshold must be exceeded before the unknown particles are assigned to a subclass, otherwise the particles are classified as background particles.

37. An apparatus for the detection and classification of particles in a sample comprising:
sensing means, including a sensing zone, for sensing characteristic features of particles;
means for moving particles of an unknown class, substantially one at a time, in a fluid flow stream through said sensing zone;
means for detecting data associated with the characteristic features of each moving particle as the particle passes through said sensing zone;
means for storing data from a plurality of known subclasses of particles each having common characteristics in accordance with a pattern of data collected from such known subclasses of particles; and
means for recognizing that sample particles from said unknown class belong to said known subclasses responsive to the recognition of said patterns by data detected from said sample particles.

38. A method for detecting biological particles of interest from a sample of an unknown class of biological particles comprising:
moving particles from a sample of unknown biological particles, substantially one at a time, in a fluid flow stream;
providing an incident beam of illumination directed at the particles in said flow stream;
detecting light-related data associated with each moving particle as the particle passes through said beam of illumination;
storing data representing a known class of particles having common characteristics based on light data collected from such known class of particles;
applying such stored data to light data detected from sample particles of said unknown class in order to match patterns between the data of the known and unknown particles; and
recognizing that particles from said unknown class belong to said known class as a result of matching patterns of respective light-related data.

39. The method of claim 38 wherein said detecting step includes detecting a plurality of different light signals.

40. The method of claim 39 wherein said detecting step includes detecting light scatter and fluorescence signals simultaneously.

41. The method of claim 40 wherein said detecting step includes detecting light scattered in at least two different directions and detecting fluorescence emitted by particles at a minimum of two different wavelengths.

42. The method of claim 38 wherein said applying step includes partitioning a space for measuring light data into a region which contains the sample particle data belonging to said known class.

43. The method of claim 42 wherein the partitioning step further includes transforming the data of said measurement space in order to cluster the sample particle data into data points representing elements of said known class.

44. The method of claim 43 wherein said transforming step transforms vectors relating to pattern data of said measurement space to a new space according to the following relationship:

$$\overline{x}' = \overline{W}\overline{x}$$

wherein:
$\overline{x}$ is the original vector of the measurement space
$\overline{x}'$ is the transformed vector
$\overline{W}$ is the transformation matrix comprised of variable weighting coefficients, $w_{ij}$.

45. The method of claim 44 wherein said transforming step includes minimizing the intraset distance between data points of the known class.

46. The method of claim 42 wherein said partitioning step includes extracting features from said stored data of the known for the discrimination of data related to said unknown particles.

47. The method of claim 46 wherein said extracting step includes extracting a plurality of features of said stored data, each feature being a linear combination of all of the original stored data measurements.

48. The method of claim 47 wherein said extracting step includes extracting uncorrelated features of said stored data when the measurements of said features are correlated in nature, whereby the mathematical form of the function which measures the correlation among the features is a covariance matrix.

49. The method of claim 48 wherein said extracting step includes transforming the stored data of the original measurement to another representation space and determining a subspace for the class which substantially preserves the data available in the original measurement space according to the following mathematical relationship:

$$\overline{C}' = \overline{W}\overline{C}\overline{W}^T$$

where
$\overline{C}'$ is the transformed covariance matrix
$\overline{C}$ is the original covariance matrix
$\overline{W}$ is the transformation matrix comprised of variable weighting coefficients, $w_{ij}$
$\overline{W}^T$ is the transposed form of the transformation matrix, $\overline{W}$.

50. A method for detecting particles in a sample comprising:
moving particles, substantially one at a time, in a fluid flow stream through a sensing zone;
detecting data associated with characteristic features of each moving particle as the particle passes through said sensing zone;
storing data from a known class of particles having common characteristics in accordance with a pattern of data collected from such known class of particles; and
recognizing that sample particles from an unknown class belong to said known class responsive to the recognition of said pattern by data detected from said sample particles.

51. A method for detecting particles in a sample comprising:
storing data from a class of particles having known, common characteristics in accordance with a pattern of data collected from such class of known particles; and
recognizing that sample particles from an unknown class belong to said known class responsive to the recognition of said pattern by data detected from said unknown sample particles.

52. A method for detecting and classifying biological particles of interest from a sample of an unknown class of biological particles comprising:
moving particles from a sample of unknown biological particles, substantially one at a time, in a fluid flow stream;
providing an incident beam of illumination directed at the particles in said flow stream;
detecting light-related data associated with each moving particle as the particle passes through said beam of illumination;
storing data representing a known class of particles having common characteristics based on said light data collected from such known class of particles;
separating data from said known class into a plurality of subclasses thereof, each subclass having its light-related data stored separately;
applying such stored data to light data detected from sample particles of said unknown class in order to match patterns between the data of the known and unknown particles; and
recognizing that particles from said unknown class belong to said known class as a result of matching patterns of respective light-related data and identifying the subclasses to which the unknown particles belong.

53. The method of claim 52 wherein said recognizing step includes numerically characterizing said subclasses by vectorial representation in a space.

54. The method of claim 53 wherein said recognizing step includes mapping particles into points and particle subclasses into clusters in a space of limited dimensionality.

55. The method of claim 54 wherein said mapping is accomplished by providing a two-dimensional presentation of four-dimensional data.

56. The method of claim 55 wherein said recognizing step includes extracting from said stored four-dimensional data those features that are most significant for classification purposes, and transforming the representation vectors of the original clusters into a new coordinate system wherein the coordinate variables are mutually uncorrelated and the data from the original clusters are concentrated in the first few axes of the new coordinate system.

57. The method of claim 52 wherein said recognizing step identifies subclasses by a statistical decision step which includes partitioning the original data storage region into a plurality of mutually exclusive and exhaustive subregions corresponding to the number of subclasses and assigning a particle to one of said subclasses if its light-related data give the largest probability in the associated subregion.

58. The method of claim 57 wherein said partitioning step includes clustering data representing subclasses of particles by encoding a set of numbers for each subclass of particles produced by two mathematical transformations, said sets each being further functionally represented by a center and a radius in the transformed space, wherein an unknown particle is identified as belonging to a known subclass if its data vector falls into the specific encoded set of numbers.

59. The method of claim 52 wherein said recognizing step for identifying subclasses includes distinguishing clusters of particles of interest from other clusters or from background particles by reliance on the data representing structure of the particles to delimit the boundary between clusters.

60. The method of claim 52 wherein said recognizing step for identifying subclasses includes examining a similarity measure defined for all pairs of points in all of the subclasses.

61. The method of claim 60 wherein said examining step includes calculating the distance between all pairs of data points and sorting the calculated values into ascending order to determing the nearest neighbors of all points, unknown particles being assigned to the subclass in which a majority of neightboring points occurs.

62. The method of claim 52 wherein the particles to be detected and classified are cells.

63. The method of claim 52 wherein the particles to be detected and classified are a plurality of subclasses of bacteria.

64. The method of claim 63 wherein the bacteria to be detected and classified are derived from a sample of biological fluid.

65. The method of claim 64 wherein the biological fluid is urine.

66. The method of claim 52 wherein the particles to be detected and classified are different subclasses of leukocytes.

67. The method of claim 52 wherein said storing step includes preparing a liquid sample with a high concentration of a known type of particles having common characteristics, and collecting and storing light data from such known class of particles to establish a region having a recognizable pattern of data points.

68. A method for detecting and classifying particles in a sample comprising:
   moving particles of an unknown class, substantially one at a time, in a fluid flow stream through a sensing zone;
   detecting data associated with characteristic features of each moving particle as the particle passes through said sensing zone;
   storing data from a plurality of subclasses of particles each having known common characteristics in accordance with patterns of data associated with such known subclasses of particles; and
   recognizing that sample particles from said unknown class belong to said known subclasses responsive to the recognition of said patterns by data associated with said sample particles.

69. A method for detecting and classifying particles in a sample comprising:
   storing data from a plurality of subclasses of particles each having known common characteristics in accordance with patterns of data associated with such known subclasses of particles; and
   recognizing that sample particles from an unknown class belong to said known subclasses responsive to the recognition of said patterns by data associated with said unknown sample particles.

* * * * *